United States Patent [19]

Nair et al.

[11] 4,359,458
[45] Nov. 16, 1982

[54] O-β.-D (AND O-α.-D) MULTIGALACTOPYRANOSYL, XYLOPYRANOSYL AND GLUCOPYRANOSYL SULFATE SALTS

[75] Inventors: Vijay G. Nair, Piermont, N.Y.; Joseph P. Joseph, Montvale, N.J.; Arthur J. Lewis, Congers; Seymour Bernstein, New City, both of N.Y.

[73] Assignee: American Cyanamid Company, Stamford, Conn.

[21] Appl. No.: 305,885

[22] Filed: Sep. 28, 1981

[51] Int. Cl.$^3$ .............. A61K 71/30; C07H 5/08; C07H 3/06; C07H 37/00
[52] U.S. Cl. .................... 424/180; 424/49; 536/1.1; 536/55.1; 536/118
[58] Field of Search .............. 424/180; 536/118, 4, 536/119, 1, 55

[56] References Cited

U.S. PATENT DOCUMENTS

| | | | |
|---|---|---|---|
| 3,356,674 | 12/1967 | Ikeda et al. | 536/4 |
| 4,021,544 | 5/1977 | Nair et al. | 536/118 |
| 4,021,545 | 5/1977 | Nair et al. | 536/118 |

Primary Examiner—Johnnie R. Brown
Attorney, Agent, or Firm—Anne M. Rosenblum

[57] ABSTRACT

O-β-D (and O-α-D) multi-galactopyranosyl (or xylopyranosyl or glucopyranosyl) $1\alpha,1\alpha'$ galactopyranosyl (or xylopyranosyl or glucopyranosyl) sulfate salts, useful as complement inhibitors, the intermediates thereof and the process for preparation of such compounds.

34 Claims, No Drawings

O-β,-D (AND O-α,-D) MULTIGALACTOPYRANOSYL, XYLOPYRANOSYL AND GLUCOPYRANOSYL SULFATE SALTS

BACKGROUND OF THE INVENTION

1. Field of Invention

The present invention relates to novel O-β-D(and O-α-D)multi-galactopyranosyl (or xylopyranosyl or glucopyranosyl)1α,1α' galactopyranosyl (or xylopyranosyl or glucopyranosyl) sulfate salts, to their use as inhibitors of the complement system of warm-blooded animals and the intermediates thereof. The invention further concerns the process for the preparation of such compounds.

2. Description of the Prior Art

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 20 proteins in the complemet system consisting of the so-called classical and alternative pathways. These complement proteins are generally designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its biochemical, biological and pathological role in the body processes can be found in, for example, Bull. W.H.O. 39: 935 (1968); Annu. Rev. Med. 19: 1 (1968); Johns Hopkins Med. J. 128: 57 (1971); Harvey Lect. 66: 75 (1972); N. Engl. J. Med. 287: 452, 489, 454, 592, 642 (1972); Sci. Am. 229 (5): 54 (1973); Fed. Proc. 32: 134 (1973): Med. World, Oct. 11, 1974, p. 53; J. Allergy Clin. Immunol. 53: 298 (1974); Cold Spring Harbor Conf. Cell Proliferation 2/ Proteases Biol. Control: 229 (1975); Annu. Rev. Biochem. 44: 697 (1975); Complement in Clinical Medicine, Dis. Mon. (1975); Complement, Scope, December 1975; Ann. Intern. Med. 84: 580 (1976); Transplant Rev.: 32 (1976); "Complement: Mechanisms and Functions," Prentice-Hall, Englewood Cliffs, N.J. (1976); Essays Med. Biochem. 2: 1 (1976); Hosp. Pract. 12: 33 (1977); Perturbation of Complement in Disease, Chap. 15 in Biol. Amplification Systems in Immunol. (Ed. Day and Good), Plenum, New York and London (1977); Am. J. Clin. Pathol. 68: 647 (1977); Biochem. Soc. Trans. 5: 1659 (1977); Harvey Lect. 72: 139 (1976-1977); J. Periodontol. 48: 505 (1977); Biochem. Soc. Trans. 6: 798 (1978); Clin. and Exp. Dermatol. 4: 271 (1979); Infect. Dis. Rev. 1: 483 (1979).

The complement system (e.g., classical pathway) can be considered to consist of three subsystems: (1) a recognition unit (C1q) which enables it to combine with antibody molecules that have detected a foreign invader; (2) an activation unit (C1r, C1s, C2, C4, C3) which prepares a site on the neighboring membrane; and (3) an attack unit (C5, C6, C7, C8 and C9) which creates a "hole" in the membrane. The membrane attack unit is nonspecific; it destorys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to host's cells. Immunity is, therefore, a double-edged sword.

Activation of the complement system also accelerates blood clotting. This action comes about by way of the complement-mediated release of a clotting factor from platelets. The biologically active complement fragments and complexes become involved in reactions that damage the host's cells. These pathogenic reactions can result in the development of immune-complex diseases. For example, in some forms of nephritis, complement damages the basal membrane of the kidney, resulting in the escape of protein from the blood into the urine. The disease disseminated lupur erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain complement proteins, suggestion regarding the mode of complement binding to biological membranes and the manner in which complement effects membrane damage are discussed in Annu. Rev. Biochem. 38: 389 (1969); J. Exp. Med. 141: 724 (1975); J. Immunol. 116: 1431 (1976); 119: 1, 1195, 1358, 1482 (1977); 120: 1841 (1978); Immunochemistry 15: 813 (1978); J. Biol. Chem. 254: 9908 (1979).

A variety of substances have been disclosed as inhibiting the complement system, i.e., as complement inhibitors. For example, the compounds 3,3'-ureylenebis [6-(2-amino-8-hydroxy-6-sulfo-1-naphthylazo)benzenesulfonic acid], tetrasodium salt (chlorazol fast pink), heparin and a sulphated dextran have been reported to have an anti-complementary effect, Br. J. Exp. Pathol. 33: 327 (1952). German Pat. No. 2,254,983 or South African Pat. No. 727, 923 discloses certain 1-(diphenylmethyl)-4-(3-phenylallyl)piperazines useful as complement inhibitors. Other chemical compounds having complement inhibiting activity are disclosed in, for example, J. Med. Chem. 12: 415, 902, 1049, 1053 (1969); Can. J. Biochem 47: 547 (1969); J. Immunol. 104: 279 (1970); J. Immunol. 106: 241 (1971); J. Immunol. 111: 1061 (1973); Biochem. Biophys. Acts 317: 539 (1973); Life Sci. 13:

351 (1973); J. Immunol. 113: 584 (1974); Immunology 26: 819 (1974); J. Med. Chem. 17: 1160 (1974); Biochem. Biophys. Res. Comm. 67: 225 (1975); Ann. N.Y. Acad. Sci. 256: 441 (1975); J. Med. Chem. 19: 634, 1079 (1976); J. Immunol. 118: 466 (1977); Arch. Int. Pharmacodyn. 226: 281 (1977); Biochem. Pharmacol. 26: 325 (1977); J. Pharm. Sci 66: 1367 (1977); Chem. Pharm. Bull. 25: 1202 (1977); Biochem. Biophys. Acta 484: 417 (1977); J. Clin. Microbiol. 5: 278 (1977); Immunochemistry 15: 231 (1978); Immunology 34: 509 (1978); J. Exp. Med. 147: 409 (1978); thromb. Res. 14: 179 (1979); J. Immunol. 122: 2418 (1979); J. Chem. Soc. Chem. Comm. 726 (1979); Immunology 36: 131 (1979): Biochem. Biophys. Acta 611: 196 (1980); and J. Med. Chem. 23: 240 (1980).

It has been reported that the known complement inhibitors, epsilon-aminocaproic acid and tranexamic acid, have been used with success in the treatment of hereditary angioneurotic edema, a disease state resulting from an inherited deficiency or lack of function of the serum inhibitor of the activated first component of complement (C1 inhibitor), N. Engl. J. Med. 286: 808 (1972): 287: 452 (1972); Ann. Intern. Med. 84: 580 (1976); J. Allergy Clin. Immunol. 60: 38 (1977). Also androgenic steroids have been used successfully in the treatment of this physiological disorder; see Medicine 58: 321 (1979); Arthritis Rheum. 22: 1295 (1979); Am. J. Med. 66: 681 (1979); and J. Allergy Clin. Immunol. 65: 75 (1980).

It has also been reported that the drug pentosan-polysulfoester has an anticomplementary activity on human serum, both in vitro and in vivo, as judged by the reduction in total hemolytic complement activity, Pathol. Biol. 25: 33; 25 (2): 105; 25 (3): 179 (1977).

SUMMARY OF THE INVENTION

The instant invention relates to new compounds of O-$\beta$-D (and O$\alpha$-D)multi-galactopyranosyl (or xylopyranosyl or glucopyranosyl) $1\alpha,1\alpha'$ galactopyranosyl (or xylopyranosyl or glucopyranosyl) sulfate salts that inhibit the complement system, thereby inhibiting complement activity in body fluids. Moreover, this invention involves a method of inhibiting the complement system in a body fluid which comprises subjecting body fluid complement to the action of an effective complement inhibiting amount of the above-identified compounds. This invention further concerns a method of inhibiting the complement system in a warm-blooded animal which comprises administering to said animal an effective complement inhibiting amount of the above-identified compounds. The invention also deals with novel precursors in the preparation of the above-described complement inhibiting compound.

DETAILED DESCRIPTION OF THE INVENTION

In accordance with the present invention, there are provided novel compounds represented by the following generic Formula I:

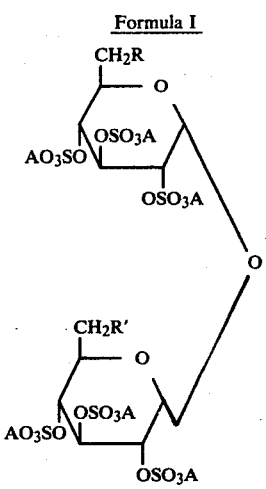

Formula I wherein A is a nontoxic pharmaceutically acceptable cation salt, wherein the salt forming moiety is selected from the group consisting of alkali metal, alkaline earth metal, ammonia and substituted ammonia selected from the group consisting of trialkylamine ($C_1$-$C_6$), piperidine, pyrazine, alkanolamine ($C_2$-$C_6$) and cycloalkylamine ($C_3$-$C_6$); R and R', when they are the same, are selected from the group consisting of

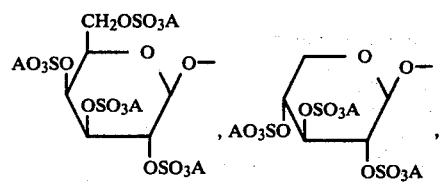

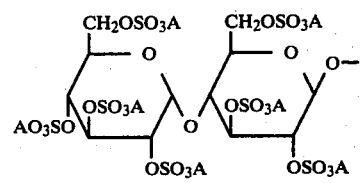

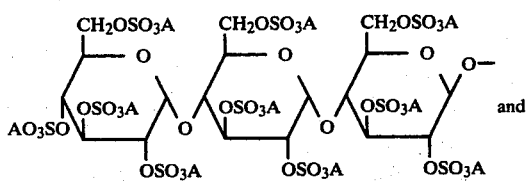

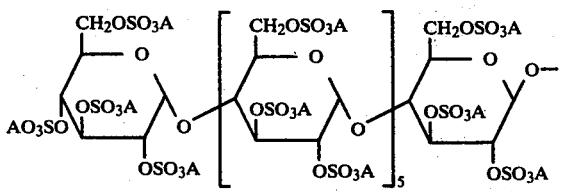

wherein A is as hereinabove defined; and R and R', when they are different, are each selected from the group consisting of —$OSO_3A$ and

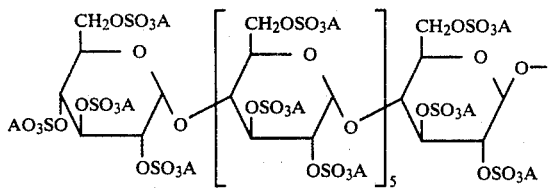

Particularly preferred compounds of this invention which are of major interest as complement inhibitors are listed below. In this instance, these compounds are named both by their full name according to Chemical Abstracts nomenclature and by an abbreviated nomenclature [in brackets] which is used throughout the balance of the specifications and claims.

O-β-D-Galactopyranosyl(1→6)-α-D-glucopyranosyl O-β-D-galactopyranosyl(1→6)-α-D-glucopyranoside, tetradecakis (H-sulfate), tetradecasalt with trimethylamine [gal 1β,6 glc 1α,1α' glc 1β,6 gal, tetradecakis (H-sulfate), tetradecasalt with trimethylamine]

O-β-D-Galactopyranosyl(1→6)-α-D-glucopyranosyl O-β-D-galactopyranosyl(1→6)-α-D-glucopyranoside, tetradecakis (H-sulfate), tetradecasodium salt [gal 1β,6 glc 1α,1α' glc 1β,6 gal, tetradecakis (H-sulfate), tetradecasodium salt]

O-β-D-Xylopyranosyl(1→6)-α-D-glucopyranosyl O-β-D-xylopyranosyl(1→6)-α-D-glucopyranoside, dodecakis (H-sulfate), dodecasalt with trimethylamine [xyl 1β,6 glc 1α,1α' glc 1β,6 xyl, dodecakis (H-sulfate), dodecasalt with trimethylamine]

O-β-D-Xylopyranosyl(1→6)-α-D-glucopyranosyl O-β-D-xylopyranosyl(1→6)-α-D-glucopyranoside, dodecakis (H-sulfate), dodecasodium salt [xyl 1β,6 glc 1α,1α' glc 1β,6 xyl, dodecakis (H-sulfate), dodecasodium salt]

O-α-D-Glucopyranosyl(1→4)-O-β-D-glucopyranosyl)(1→6)-α-D-glucopyranosyl O-α-D-glucopyranosyl(1→4)-O-β-D-glucopyranosyl(1→6)-α-D-glucopyranoside, eicosakis (H-sulfate), eicosasalt with trimethylamine [glc 1α,4 glc 1β,6 glc 1α,1α' glc 1β,6 glc 1α,4 glc, eicosakis (H-sulfate), eicosasalt with trimethylamine]

O-α-D-Glucopyranosyl(1→4)-O-β-D-glucopyranosyl(1→6)-α-D-glucopyranosyl O-α-D-glucopyranosyl(1→4)-O-β-D-glucopyranosyl (1→6)-α-D-glucopyranoside, eicosakis (H-sulfate), eicosasodium salt [glc 1α,4 glc 1β,6 glc 1α,1α' glc 1β,6 glc 1α,4 glc, eicosakis (H-sulfate), eicosasodium salt]

O-α-D-Glucopyransoyl(1→4)-O-α-D-glucopyranosyl(1→4)-O-β-D-glucopyranosyl(1→6)-α-D-glucopyranosyl O-α-D-glucopyranosyl (1→4)-O-α-D-glucopyranosyl(1→4)-O-β-D-glucopyranosyl (1→6)-α-D-glucopyranoside, hexacosakis (H-sulfate), hexacosasalt with trimethylamine [glc 1α,4 glc 1α,4 glc 1β, 6 glc 1α,1α' glc 1β, 6 glc 1α,4 glc 1α,4 glc, hexacosakis (H-sulfate) hexacosasalt with trimethylamine]

O-α-D-Glucopyranosyl)(1→4)-O-α-D-glucopyranosyl(1→4)-O-β-D-glucopyranosyl(1→6)-α-D-glucopyranosyl O-α-D-glucopyranosyl (1→4)-O-α-D-glucopyranosyl(1→4)-O-β-D-glucopyranosyl (1→6)-α-D-gluocpyranoside, hexacosakis (H-sulfate), hexacosasodium salt[glc 1α,4 glc 1α,4 glc 1β,6 glc 1α,1α' glc 1β,6 glc 1α,4 glc 1α,4 glc, hexacosakis (H-sulfate), hexacosasodium salt]

O-α-D-Glucopyranosyl(1→4)-O-α-D-glucopyrasnoyl(1→4)-O-α-D-glucopyranosyl(1→4)-O-α-D-glucopyranosyl(1→4)-O-α-D-glucopyranosyl(1→4)-O-α-D-glucopyranosyl(1→4)-O-β-D-glucopyranosyl(1→6)-α-D-glucopyranosyl O-α-D-Glucopyranosyl-(1→4)-O-α-D-glucopyransoyl(1→4)-O-α-D-glucopyranosyl(1→4)-O-α-D-glucopyranosyl(1→4)-O-α-D-glucopyranosyl(1→4)-O-α-D-glucopyranosyl(1→4)-O-α-D-glucopyransoyl(1→4)-O-β-D-glucopyranosyl(1→6)-α-D-glucopyranoside, pentacontakis (H-sulfate), pentacontasalt with trimethylamine [glc 1α,4 (glc 1α,4)5 glc 1β,6 glc 1α,1α' glc 1β,6 glc (glc 1α,4)5 1α,4 glc, pentacontakis (H-sulfate), pentacontasalt with trimethylamine]

O-α-D-Glucopyranosyl(1→4)-O-α-D-glucopyranosyl(1→4)-O-α-D-glucopyranosyl(1→4)-O-α-D-glucopyranosyl(1→4)-O-α-D-glucopyranosyl(1→4)-O-α-D-glucopyranosyl(→4)-O-β-glucopyranosyl(1→6)-α-D-glucopyranosyl O-α-D--glucopyranosyl(1→4)-O-α-D-glucopyranosyl(1→4)-O-α-D-glucopyranosyl(1→4)-O-α-D-glucopyranosyl(1→4)-O-α-D-glucopyranosyl(1→4)-O-β-D-glucopyranosyl(1→6)-α-D-glucopyranoside, pentacontakis (H-sulfate), pentacontasodium salt [glc 1α,4 (glc 1α,4)5 glc 1β,6 glc 1α,1α' glc 1β,6 glc (glc 1α,4)5 1α,4 glc, pentacontakis (H-sulfate), pentacontasodium salt]

O-α-D-Glucopyranosyl(1→4)-O-α-D-glucopyranosyl(1→4)-O-α-D-glucopyranosyl(1→4)-O-α-D-glucopyranosyl(1→4)-O-α-D-glucopyranosyl(1→4)-O-β-D-glucopyranosyl(1→6)-O-α-D-glucopyranosyl-α-D-glycopyranoside, nonacosakis (H-sulfate), nonacosasalt with trimethylamine [glc 1α,4 (glc 1α,4)5 glc 1β,6 glc 1α,1α' glc, nonacosakis (H-sulfate), nonacosasalt with trimethylamine]

O-α-D-Glucopyranosyl(1→4)-O-α-D-glucopyranosyl(1→4)-O-α-D-glucopyranosyl(1→4)-O-α-D-glucopyranosyl(1→4)-O-α-D-glucopyranosyl(1→4)-O-β-D-glucopyranosyl(1→6)-O-α-D-glucopyranosyl-α-D-glucopyranoside, nonacosakis (H-sulfate), nonacosasodium salt [glc 1α,4 (glc 1α,4)5 glc 1β,6 glc 1α,1α' glc, nonacosakis (H-sulfate), nonacosasodium salt].

This invention further deals with a method of inhibiting the complement system in a body fluid, such as blood serum, which comprises subjecting body fluid complement to the action of an effective complement inhibiting amount of a compound of the above formula. Body fluids can include blood, plasma, serum, synovial fluid, cerebrospinal fluid, or pathological accumulation of fluid such as pleural effusion, etc. The invention also concerns a method of inhibiting the complement system in a warm-blooded animal which comprises administering to said warm-blooded animal an effective complement inhibiting amount of a compound of the above formula.

The compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of autoallergic hemolytic anemia, certain kinds of platelet disorders and certain kinds of vasculitis. These compounds may also be used in the therapeutic treatment of warm-blooded animals having non-immunologic diseases such as paroxysmal nocturnal hemoglobinurea, hereditary angioneurotic edema (such as Suramin Sodium, etc.) and inflammatory states induced by the action of bacterial or lysosomal enzymes on the appropriate complement components as, for example, inflammation following coronary occlusion. They may also be useful in the treatment of transplant rejection and ulcers and as blood culture and transport mediums.

In addition, this invention is concerned with the compounds of the following Formula II, which are intermediates for the preparation of the compounds of Formula I:

FORMULA II

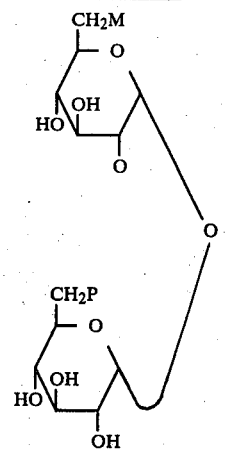

wherein M and P, when they are the same, are selected from the group consisting of

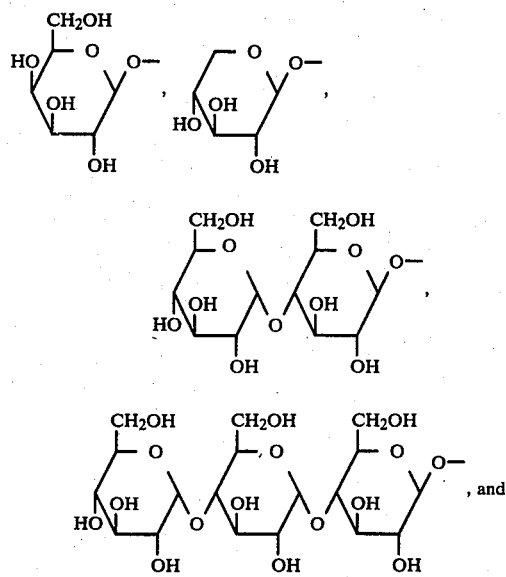

, and

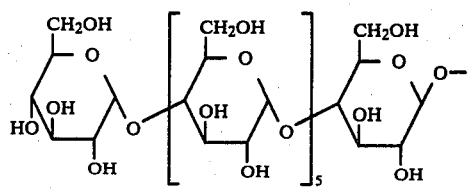

and M and P, when they are different, are each selected from the group consisting of OH and

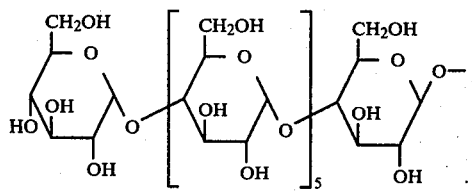

Specific compounds of the above Formula II which are of particular interest as intermediates are listed below. As before, these compounds are given both by their full name, according to Chemical Abstracts nomenclature, and by an abbreviated nomenclature [in brackets] which is used throughout the balance of the specification and claims.

O-β-D-Galactopyranosyl(1→6)-α-D-glucopyranosyl O-β-D-galactopyranosyl(1→6)-α-D-glucopyranoside [gal 1β,6 glc 1α, 1α′ glc 1β,6 gal]

O-β-D-Xylopyranosyl(1→6)-α-D-glucopyranosyl O-β-D-xylopyranosyl(1→6)-α-D-glucopyranoside [xyl 1β,6 glc 1α,1α′ glc 1β,6 xyl]

O-α-D-Glucopyranosyl(1→4)-O-β-D-glucopyranosyl(1→6)-α-D-glucopyranosyl O-α-D-glucopyranosyl(1→4)-O-β-D-glucopyranosyl(1→6)-α-D-glucopyranoside [glc 1α,4 glc 1β,6 glc 1α,1α′ glc 1β,6 glc 1α,4 glc]

O-α-D-Glucopyranosyl(1→4)-O-α-D-glucopyranosyl(1→4)-O-β-D-glucopyranosyl(1→6)-glucopyranosyl O-α-D-glucopyranosyl (1→4)-O-α-D-glucopyranosyl(1→4)-O-β-D-glucopyranosyl(1→6)-α-D-glucopyranoside [glc 1α,4 glc 1α,4 glc 1β,6 glc 1α,1α′ glc 1β,6 glc 1α,4 glc 1α,4 glc]

O-α-D-Glucopyranosyl(1→4)-O-α-D-glucopyranosyl(1→4)-O-α-D-glucopyranosyl(1→4)-O-α-D-glucopyranosyl(1→4)-O-α-D-glucopyranosyl(1→4)-O-β-D-glucopyranosyl(1→6)-α-D-glucopyranosyl O-α-D-glucopyranosyl(1→4)-O-α-D-glucopyranosyl(1→4)-O-α-D-glucopyranosyl(1→4)-O-α-D-glucopyranosyl(1→4)-O-α-o-glucopyranosyl(1→4)-O-β-D-glucopyranosyl(1→6)-α-D-glucopyranoside [glc 1α,4 (glc 1α,4)₅ glc 1β,6 glc 1α,1α′ glc 1β,6 glc (glc 1α,4)₅ 1α,4 glc]

O-α-D-Glucopyranosyl(1→4)-O-α-D-glucopyranosyl(1→4)-O-α-D-glucopyranosyl(1→4)-O-α-D-glucopyranosyl(1→4)-O-α-d-glucopyranosyl(1→4)-O-α-D-glucopyranosyl(1→4)-O-β-glucopyranosyl(1→6)-O-α-D-glucopyranosyl-α-D-glucopyranoside [glc 1α,4 (glc 1α,4)₅ glc 1β,6 glc 1α,1α′ glc].

The compounds of the present invention may be prepared according to the following flowchart:

Flowchart
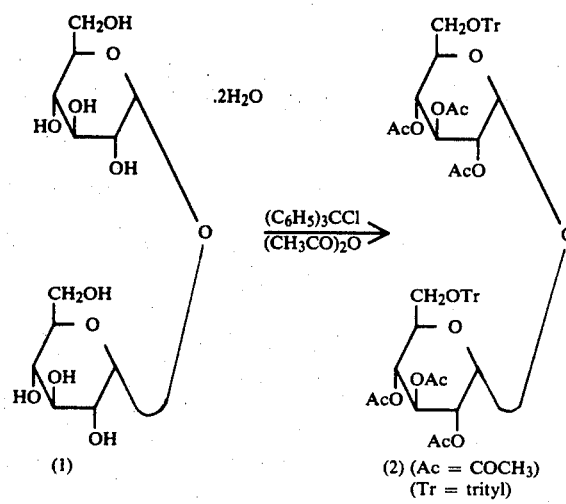
(1)        (2) (Ac = COCH$_3$)
(Tr = trityl)
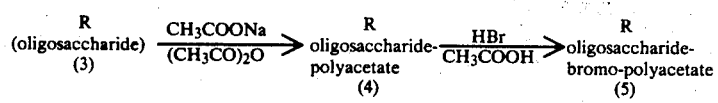
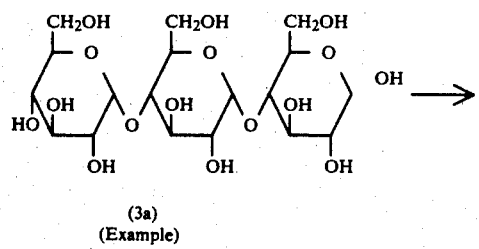
(3a)
(Example)
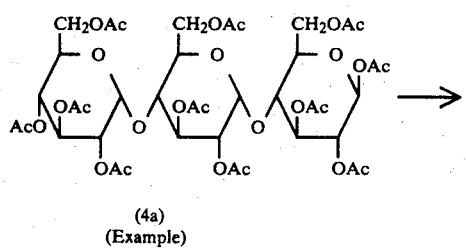
(4a)
(Example)
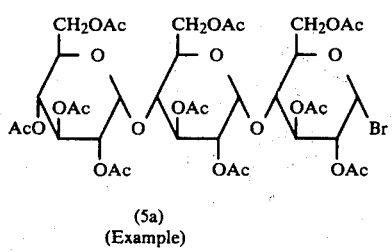
(5a)
(Example)

-continued
Flowchart
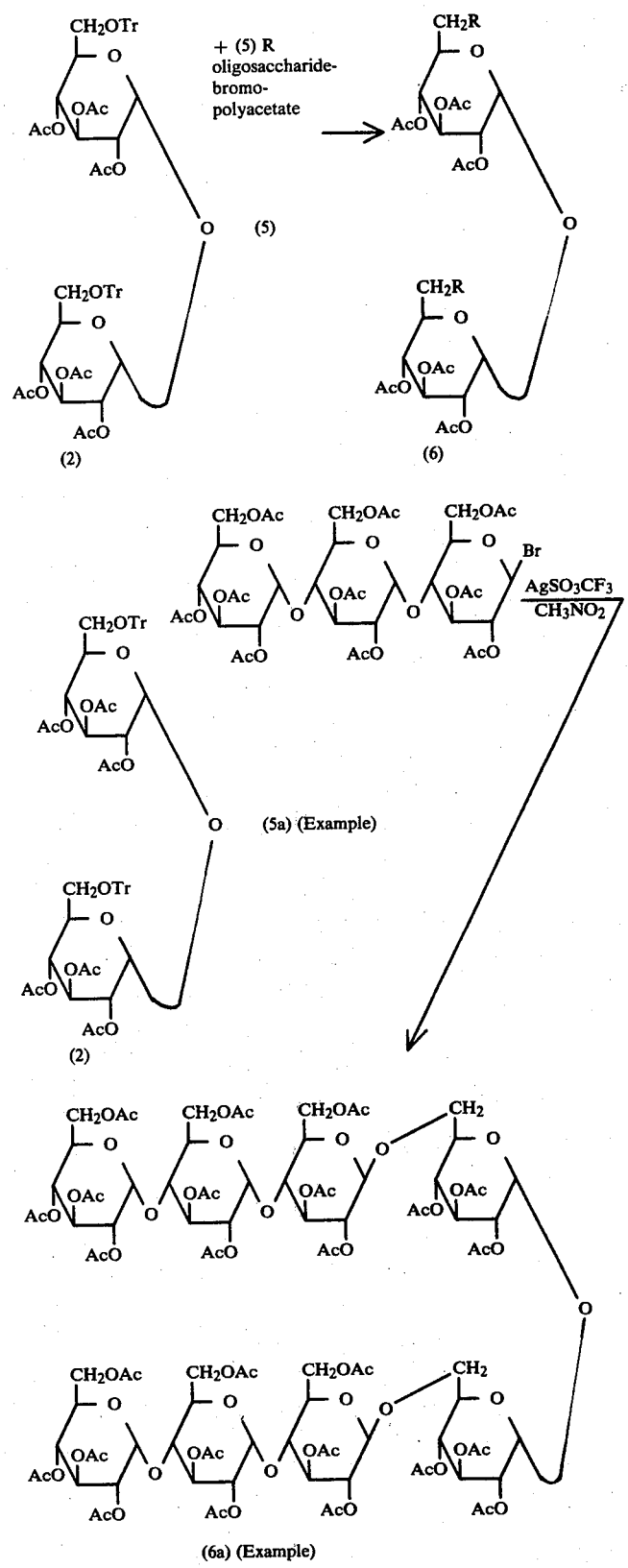

-continued
Flowchart
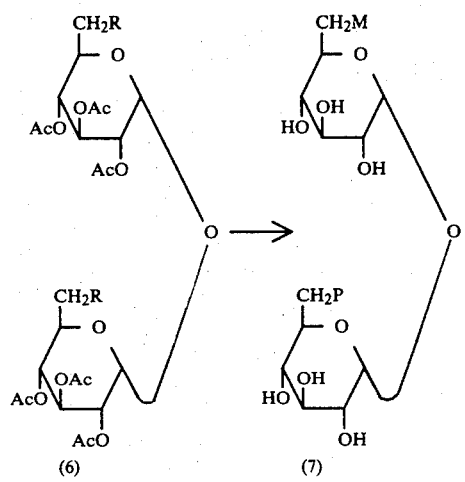
(6) (7)
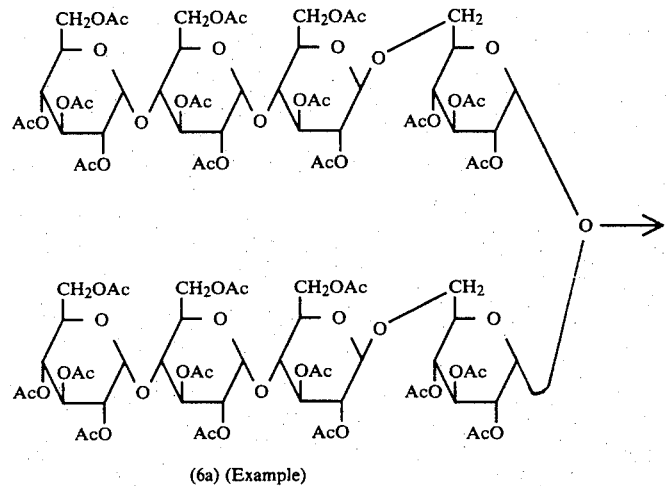
(6a) (Example)
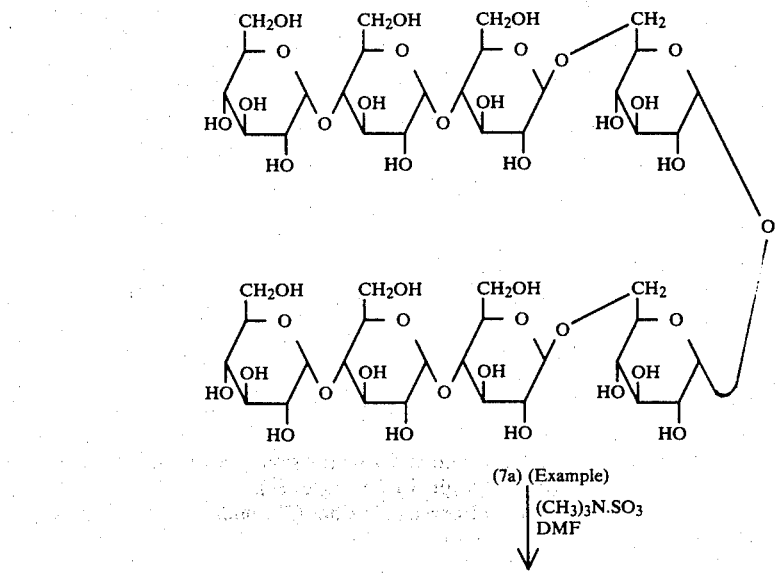
(7a) (Example)
| (CH₃)₃N·SO₃
| DMF
↓

-continued
Flowchart

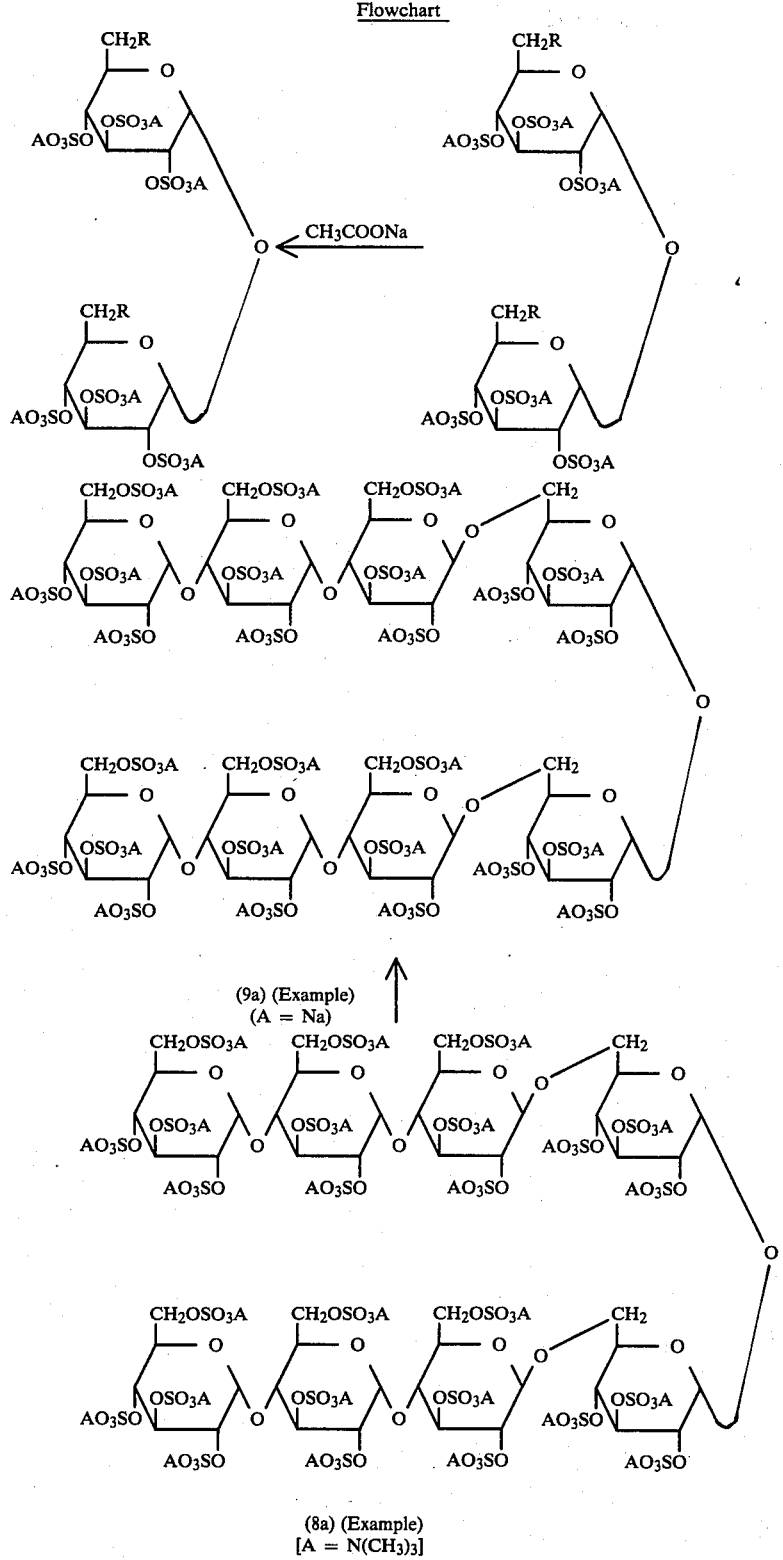

(9a) (Example)
(A = Na)

(8a) (Example)
[A = N(CH₃)₃]

In accordance with the above flowchart, [glc 1α,1α' glc dihydrate] (1) in pyridine containing anhydrous calcium sulfate is heated at 95°–100° C. for 2–6 hours. Trityl chloride is added, heating is continued for 1–3 hours and acetic anhydride is added. The mixture is added to ice and water giving a precipitate of [ditrityl peracetyl glc 1α,1α' glc] (2).

An oligosaccharide (3), such as maltotriose (3a), where R is

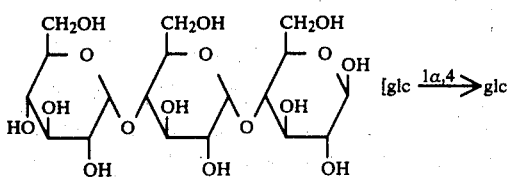

is treated with anhydrous sodium acetate and acetic anhydride [Carbohydrate Chemistry 1:338 (1962)] giving an oligosaccharide-polyacetate (4) (eg.(4a)

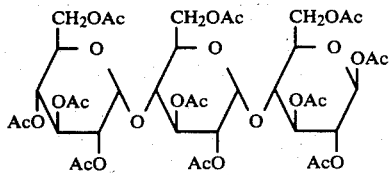

where Ac is acetate, [glc 1α,4 glc 1α,4 glc undecaacetate]), which is then reacted with a solution of hydrogen bromide in glacial acetic acid, after solubilizing in dichloromethane, at ice bath temperature for several hours. The reaction is quenched in ice and water and extracted with chloroform which is evaporated giving the oligosaccharide-bromo-polyacetate (5) (eg. (5a)

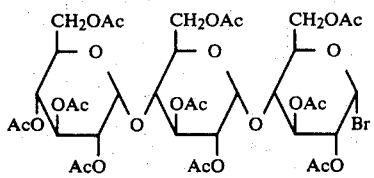

where Ac is acetate, [acetobromo glc 1α,4 glc 1α,4 glc]).

The [ditrityl peracetyl glc 1α,1α′ glc] (2) is added to a cooled solution of silver triflate and anhydrous calcium sulfate in nitromethane. The oligosaccharide-bromo-polyacetate [eg. (5a) acetobromo glc 1α,4 glc 1α,4 glc] is added, the mixture is stirred, diluted with dichloromethane and filtered. The filtrate is evaporated and the residue is treated with acetic anhydride is pyridine for 18-24 hours and then poured into ice and water. The solid is extracted in dichloromethane and purified by conventional chromatography on silica gel giving the polyacetate of the compounds of this invention (6) [eg. (6a) glc 1α,4 glc 1α,4 glc 1β,6 glc 1α,1α′ glc 1β,6 glc 1α,4 glc 1α,4 glc, hexacosaacetate].

The polyacetate sugar (6) [eg. (6a)] is dissolved in a 3:2:6 mixture of triethylamine-water-methanol, stirred for 18-24 hours, evaporated and recrystallized from water giving the sugars (7) [eg. (7a) glc 1α,4 glc 1α,4 glc 1β,6 glc 1α,1α′ glc 1β,6 glc 1α,4 glc 1α,4 glc] which are considered to be intermediates in the preparation of the compounds of this invention and where M and P are as described above.

The basic sugar (7) is treated with trimethylamine-sulfur trioxide in dimethylformamide at 65°-70° C. for 18-24 hours and extracted with ethanol giving the trimethylamine salt (8) [eg. (8a) glc 1α,4 glc 1α,4 glc 1β,6 glc 1α,1α′ glc 1β,6glc 1α,4 glc 1α,4 glc, hexacosakis (H-sulfate), hexacosasalt with trimethylamine] which in turn may be treated with 30% aqueous sodium acetate solution at room temperature and then extracted with ethanol giving the sodium salt (9) [eg. (9a) glc 1α,4 glc 1β,6 glc 1α,1α′ glc 1β,6 glc 1α,4 glc 1α,4 glc, hexacosakis (H-sulfate), hexacosasodium salt].

It is generally preferred that the respective product of each process step, described hereinabove, is separated and/or isolated prior to its use as starting material for subsequent steps. Separation and isolation can be effected by any suitable purification procedure such as, for example, evaporation, crystallization, column chromatography, thin-layer chromatography, distillation, etc. Also, it should be appreciated that when typical reaction conditions (e.g., temperatures, mole ratios, reaction times) have been given, the conditions which are both above and below these specified ranges can also be used, though generally less conveniently.

The term "pharmaceutically acceptable salts" refers to those salts of the parent compound which do not significantly or adversely affect the pharmaceutical properties (e.g., toxicity, effectiveness, etc.) of the parent compound. The salts of the present invention which are pharmaceutically acceptable include the alkali metals (e.g., sodium, potassium, etc); alkaline earth metals (e.g., calcium, etc.); ammonia; and substituted ammonia selected from the group consisting of trialkylamine ($C_1$-$C_6$), piperidine, pyrazine, alkanolamine ($C_2$-$C_6$) and cycloalkylamine ($C_3$-$C_6$).

The term "trialkylamine ($C_1$-$C_6$)" defines those amines having three aliphatic fully saturated hydrocarbon substituents containing 1 to 6 carbon atoms either linearly or branched. Typically, these amines are trimethylamine, triethylamine, tripropylamine, dimethylethylamine, dimethyl-1-propylamine, etc. The term "alkanolamine ($C_2$-$C_6$)" refers to the above-defined trialkylamines additionally substituted with at least one and not more than three hydroxy groups on at least two of the alkyl hydrocarbon chains. Such amines are, for example, triethanolamine, tripropanolamine, etc. The term "cycloalkylamine ($C_3$-$C_6$)" is defined as the 3 to 6 fully saturated carbocyclic moieties such as cyclopropyl, methylcyclobutyl, cyclopentyl, cyclohexyl, etc.

As used hereinabove and below unless expressly stated to the contrary, all temperatures and temperature ranges refer to the centigrade system and the terms "ambient" or "room temperature" refer to about 20° C. The term "percent" or "(%)" refers to weight percent and the terms "mole" and "moles" refer to gram moles. The term "equivalent" refers to a quantity of reagent equal in moles to the moles of the preceding or succeeding reactant recited in the preparation or Example in the term of moles of finite weight or volume.

A further understanding of the invention can be obtained from the following non-limiting Preparations and Examples.

EXAMPLE 1

[Gal 1β,6 glc 1α,1α′ glc 1β,6 gal, tetradecaacetate]

A 9.5 g portion of [glc 1α,1α′ glc dihydrate] is dissolved in 100 ml of pyridine and 10 g of anhydrous calcium sulfate are added. The mixture is stirred in an oil bath at 95°-100° C. for 4 hours. A 16.7 g portion of trityl chloride is added and the heating is continued for 2 hours. A 50 ml portion of acetic anhydride is added, the reaction mixture is cooled to room temperature and stirred overnight. The mixture is filtered and the filtrate is poured into ice water with vigorous stirring. The precipitate is collected by filtration, washed with water and dried, giving [ditrityl peracetyl glc 1α,1α′ glc] as a pale pink granular solid.

A 3.1 g portion of silver triflate (silver trifluoromethanesulfonate) is added to 100 ml of nitromethane containing 10 g of anhydrous calcium sulfate. The mixture is cooled in an ice bath and 5.4 g of [ditrityl peracetyl glc 1α,1α' glc] is added with stirring for 5 minutes. A 4.9 g portion of acetobromogalactose is added and the mixture is stirred in the ice bath for 45 minutes. The mixture is then warmed on a steam bath for 2 minutes, cooled, diluted with 150 ml of dichloromethane and filtered. The filtrate is washed with water, then with saturated aqueous sodium bicarbonate solution, dried over anhydrous sodium sulfate and the solvent is evaporated in vacuo, leaving a pale cream-colored solid. This solid (7.2 g) is dissolved in 30 ml of pyridine and 25 ml of acetic anhydride are added. The mixture is stirred at room temperature for 20 hours, then poured into ice water. The gummy product is isolated, dissolved in dichloromethane, dried over anhydrous sodium sulfate and the solvent evaporated in vacuo, giving 8.5 g of a pale brown glass. This crude product is purified by conventional chromatography on silica gel giving the desired product.

EXAMPLE 2

[Gal 1β,6 glc 1α,1α' glc 1β,6 gal]

A 2.1 g portion of [gal 1β,6 glc 1α,1α' glc 1β,6 gal tetradecaacetate] is dissolved in 33 ml of a mixture of triethylamine-water-methanol (3:2:6) and stirred at room temperature for 20 hours. The solution is evaporated to a gum and then redissolved in 20 ml of water, treated with a small amount of Amberlite® IR-120 (H+ form) and charcoal and filtered through a bed of diatomaceous earth with a small amount of charcoal. The filtrate is evaporated to dryness in vacuo, giving the desired product as a colorless glass.

EXAMPLE 3

[Gal 1β,6 glc 1α,1α' glc 1β,6 gal, tetradecakis (H-sulfate), tetradecasalt with trimethylamine]

A 4.6 g portion of trimethylamine-sulfur trioxide is added to 20 ml of dimethylformamide and the mixture is stirred and heated in an oil bath until a clear solution is obtained. A 900 mg portion of [gal 1β,6 glc 1α,1α' glc 1β,6 gal] is added and stirring is continued at 65°-70° C. for 20 hours. The gum which forms is collected by decantation and triturated with absolute ethanol giving a solid which is collected by filtration, washed with ethanol, then ether and dried in vacuo, giving the desired product as a colorless powder.

EXAMPLE 4

[Gal 1β,6 glc 1α,1α' glc 1β,6 gal, tetradecakis (H-sulfate), tetradecasodium salt]

A 2.5 g portion of [gal 1β,6 glc 1α,1α' glc 1β,6 gal, tetradecakis (H-sulfate), tetradecasalt with trimethylamine] is dissolved in 10 ml of water and 10 ml of 30% aqueous sodium acetate solution are added. The mixture is allowed to stand at room temperature for 20 minutes and then 100 ml of absolute ethanol are added. The gummy product which forms is collected by decantation, redissolved in 5 ml of water and 2 ml of 30% aqueous sodium acetate solution is added. A 100 ml portion of absolute ethanol is added, the solid is collected, triturated with absolute ethanol, collected by filtration, washed with absolute ethanol, then ether and dried in vacuo, giving the desired product as a colorless granular solid.

EXAMPLE 5

[Xyl 1β,6 glc 1α,1α' glc 1β,6 xyl, dodecaacetate]

A 5.0 g portion of anhydrous calcium sulfate and 1.54 g of silver triflate are taken up in 40 ml of nitromethane and stirred in an ice bath. To this is added 2.2 g of [ditrityl peracetyl glc 1α,1α' glc] with stirring for 5 minutes followed by 2.03 g of acetobromo-α-D-xylopyranose [Carbohydrate Chemistry 1:183 (1962)], with stirring for 45 minutes. The procedure of Example 1 is followed giving the desired product as a pale yellow granular solid.

EXAMPLE 6

[Xyl 1β,6 glc 1α,1α' glc 1β,6 xyl]

A 3.5 g portion of [xyl 1β,6 glc 1α,1α' glc 1β,6 xyl, dodecaacetate] is dissolved in 55 ml of a mixture of methanol-water-triethylamine (6:2:3). The procedure of Example 2 is followed, giving the desired product as a colorless glass.

EXAMPLE 7

[Xyl 1β,6 glc 1α,1α' glc 1β,6 xyl, dodecakis (H-sulfate), dodecasalt with trimethylamine]

A 1.5 g portion of [xyl 1β,6 glc 1α,1α' glc 1β,6 xyl], 7.31 g of trimethylamine-sulfur trioxide and 40 ml of dimethylformamide are reacted as described in Example 3, giving the desired product as a colorless powder.

EXAMPLE 8

[Xyl 1β,6 glc 1α,1α' glc 1β,6 xyl, dodecakis (H-sulfate), dodecasodium salt]

A 4.1 g portion of [xyl 1β,6 glc 1α,1α' glc 1β,6 xyl, dodecakis (H-sulfate), dodecasalt with trimethylamine], 15 ml of 30% aqueous sodium acetate solution and 20 ml of water are reacted as described in Example 4, giving the desired product as a colorless powder.

EXAMPLE 9

[Glc 1α,4 glc 1β,6 glc 1α,1α' glc 1β,6 glc 1α,4 glc, eicosaacetate]

A suspension of 50.0 g of anhydrous sodium acetate in 500 ml of acetic anhydride is heated to boiling and 100 g of [glc 1α,4 glc] is added portionwise with caution to keep the mixture gently boiling. After the addition is complete the mixture is boiled vigorously, cooled to about 50° C. and poured into 2 liters of vigorously stirred ice and water. The resulting solid is separated by decantation and fresh ice and water are added. The mixture is allowed to stand 4 hours and the solid is collected by filtration, dissolved in 200 ml of dichloromethane, washed with water, excess sodium bicarbonate solution, then twice with water, dried over sodium sulfate, filtered through hydrous magnesium silicate, washed with dichloromethane and evaporated to a gum. Ethanol is added, the mixture is reconcentrated, then dissolved in 200 ml of ethanol and cooled. The solid is collected and recrystallized twice from ethanol, giving 56.0 g of [glc 1α,4 glc, octaacetate], m.p. 158°-160° C.

A 28.0 g portion of [glc 1α,4 glc octaacetate] is dissolved by stirring in a 0°-5° C, 30% solution of hydrobromic acid in acetic acid for 3 hours. The solution is diluted with 300 ml of chloroform and then washed with ice water until no longer acid to Congo Red paper. The chloroform layer is separated, dried over sodium sulfate, filtered and evaporated to a white glass, giving 33.0 g of [acetobromo glc 1α,4 glc].

A 15 g portion of [ditrityl peracetyl glc 1α,1α' glc] is dissolved in 150 ml of nitromethane and 3 g of anhydrous calcium sulfate are added. To this is added 12.9 g of silver fluorosulfonate, the mixture is cooled to 0°–5° C. and a solution of 33 g of [acetobromo glc 1α,4 glc] in 50 ml of nitromethane is added. The mixture is stirred at 0°–5° C. for one hour, warmed for a few minutes, cooled, filtered and the filtrate diluted with 250 ml of dichloromethane. This solution is washed with cold water, saturated sodium bicarbonate solution, then twice with water, dried over magnesium sulfate, filtered and evaporated to a gum. This gum is dissolved in 50 ml of pyridine, 25 ml of acetic anhydride is added and the mixture is allowed to stand at room temperature overnight. The mixture is poured into 3 liters of ice and water and stirred for one hour. The solid is recovered by filtration and washed three times with water giving crude [glc 1α,4 glc 1β,6 glc 1α,1α' glc 1β,6 glc 1α,4 glc, eicosaacetate] which is purified by conventional chromatography.

EXAMPLE 10

[Glc 1α,4 glc 1β,6 glc 1α,1α' glc 1β,6 glc 1α,4 glc]

A 10 ml portion of methanol is saturated at 0° C. with ammonia. A 180 mg portion of [glc 1α,4 glc 1β,6 glc 1α,1α' glc 1β,6 glc 1α,4 glc, eicosaacetate] is dissolved in the above solution which is then allowed to stand at room temperature for 18 hours. The solvent is removed in vacuo and the residue is triturated with absolute ethanol and ether giving a gummy solid. This solid is dissolved in 0.5 ml of water, a small amount of ethanol is added and the cloudy solution is filtered through diatomaceous earth. Absolute ethanol is added to the filtrate and the resulting solid is collected, washed with absolute ethanol, then ether and dried in vacuo, giving the desired product.

EXAMPLE 11

[Glc 1α,4 glc 1β,6 glc 1α,1α' glc 1β,6 glc 1α,4 glc, eicosakis (H-sulfate), eicosasalt with trimethylamine]

A 0.5 g portion of [glc 1α,4 glc 1β,6 glc 1α,1α' glc 1β,6 glc 1α,4 glc] is dissolved in 5 ml of dimethylformamide, 1.53 g of trimethylamine-sulfur trioxide is added and the procedure of Example 3 is followed, giving the desired product.

EXAMPLE 12

[Glc 1α,4 glc 1β,6 glc 1α,1α' glc 1β,6 glc 1α,4 glc, eicosakis (H-sulfate), eicosasodium salt]

A 1.0 g portion of [glc 1α,4 glc 1β,6 glc 1α,1α' glc 1β,6 glc 1α,4 glc, eicosakis (H-sulfate), eicosasalt with trimethylamine] is dissolved in 5 ml of water, 2.5 ml of 30% aqueous sodium acetate is added and the procedure of Example 4 is followed, giving the desired product as a white solid.

EXAMPLE 13

[Glc 1α,4 glc 1α,4 glc 1β,6 glc 1α,1α' glc 1β,6 glc 1α,4 glc 1α,4 glc, hexacosaacetate]

A 25 g portion of [glc 1α,4 glc 1α,4 glc] 15 g of anhydrous sodium acetate and 150 ml of acetic anhydride are reacted as described in Carbohydrate Chemistry 1:338 (1962), giving glc 1α,4 glc 1α,4 glc undecaacetate.

A 40 ml portion of 32% hydrogen bromide in glacial acetic acid is cooled in an ice bath. A solution of 10.5 g of [glc 1α,4 glc 1α,4 glc undecaacetate] in 60 ml of dichloromethane is added with swirling and the mixture is allowed to stand in the ice bath with occasional swirling for 2 hours. The mixture is poured into crushed ice with vigorous swirling and extracted into 100 ml of chloroform. The aqueus layer is washed with two 75 ml portions of chloroform. The combined extract and washings are washed with five 250 ml portions of ice-cold water until neutral, dried over calcium chloride and evaporated to dryness in vacuo giving [acetobromo glc 1α,4 glc 1α,4 glc] as a colorless glass.

A 2.68 g portion of silver triflate, 10 g of anhydrous calcium sulfate, 75 ml of nitromethane, 4.32 g of [ditrityl peracetyl glc 1α,1α' glc] and 8.9 g of [acetobromo glc 1α,4 glc 1α,4 glc] are reacted as described in Example 1, giving a pale yellow glassy solid which is acetylated with 50 ml of acetic anhydride in 70 ml of pyridine as described in Example 1, giving the desired product.

EXAMPLE 14

[Glc 1α,4 glc 1α,4 glc 1β,6 glc 1α,1α' glc 1β,6 glc 1α,4 glc 1α,4 glc]

A 2.5 g portion of [glc 1α,4 glc 1α,4 glc 1β,6 glc 1α,1α' glc 1β,6 glc 1α,4 glc 1α,4 glc, hexacosaacetate] in 55 ml of a mixture of methanol-water-triethylamine is treated as described in Example 2, giving the desired product as a colorless glass.

EXAMPLE 15

[Glc 1α,4 glc 1α,4 glc 1β,6 glc 1α,1α' glc 1β,6 glc 1α,4 glc 1α,4 glc, hexacosakis (H-sulfate), hexacosasalt with trimethylamine]

A 985 mg portion of [glc 1α,4 glc 1α,4 glc 1β,6 glc 1α,1α' glc 1β,6 glc 1α,4 glc 1α,4 glc] and 2.56 g of trimethylamine-sulfur trioxide in 20 ml of dry dimethylformamide are reacted as described in Example 3, giving the desired product as a colorless granular solid.

EXAMPLE 16

[Glc 1α,4 glc 1α,4 glc 1β,6 glc 1α,1α' glc 1β,6 glc 1α,4 glc 1α,4 glc, hexacosakis (H-sulfate), hexacosasodium salt]

A 2.8 g portion of [glc 1α,4 glc 1α,4 glc 1β,6 glc 1α,1α' glc 1β,6 glc 1α,4 glc 1α,4 glc, hexacosakis (H-sulfate), hexacosasalt with trimethylamine], 10 ml of 30% aqueous sodium acetate solution and 15 ml of water are reacted as described in Example 4, giving the desired product as a colorless granular solid.

EXAMPLE 17

[Glc 1α,4 (glc 1α,4)5 glc 1β,6 glc 1α,1α' glc nonacosaacetate and glc 1α,4 (glc 1α,4)5 glc 1β,6 glc 1α,1α' glc 1β,6 glc (glc 1α,4)5 1α,4 glc pentacontaacetate]

A 10 g portion of β-cyclodextrin is added in four increments of 2.5 g each, at 10 minute intervals to a refluxing mixture of 5.0 g of sodium acetate in 50 ml of acetic anhydride, with stirring. Refluxing and stirring is continued for 30 minutes, then the mixture is cooled to room temperature and, before crystallization occurs, the solution is poured into 800 ml of ice and water. After stirring for 4–5 hours the solid is recovered by filtration, washed with 2 liters of cold water and dried in vacuo at room temperature for 3 hours. This solid is dissolved in 300 ml of hot toluene, dried over magnesium sulfate, filtered and the toluene is removed at 50° C. in vacuo on a rotary evaporator. The gummy residue is dissolved in 120 ml of methanol with heat and then allowed to crystallize out overnight. The solid is collected and dried at 35° C. in vacuo giving 15.07 g of β-cyclodextrin heneicosaacetate as a white crystalline solid.

A 10.0 g portion of β-cyclodextrin heneicosaacetate is dissolved in 30 ml of glacial acetic acid and then 50 ml of 30-32% hydrogen bromide in glacial acetic acid containing 400 mg of red phosphorous is added. The mixture is stirred briskly for 50 minutes at room temperature then the reaction is stopped by the addition of 300 ml of chloroform. The mixture is washed with three 300 ml portions of aqueous sodium acetate solution, followed by two 200 ml portions of water, dried over magnesium sulfate and evaporated in vacuo. The residue is taken up in a minimum of chloroform and added dropwise to 200 ml of vigorously stirred petroleum ether (b.p. 35°-60° C.). The resulting white precipitate is collected by filtration, washed with petroleum ether and dried in vacuo giving 9.57 g of a white amorphous solid.

A mixture of 9.35 g of the above amorphous solid and 5.3 g of silver carbonate in 25 ml of acetone containing 0.5 ml of water is stirred at room temperature for 3 hours. The silver carbonate is removed by filtration through a borosilicate filter pad, washing with 250 ml of acetone. The acetone is evaporated in vacuo and 150 ml of pyridine followed by 100 ml of acetic anhydride are added to the residue. The acetylation is allowed to proceed at room temperature for 18 hours then the reaction mixture is added dropwise to 2 liters of ice and water with stirring. After standing for 2 hours the solid is recovered by filtration, washed with one liter of cold water and dried overnight at room temperature, giving a white amorphous powder. This powder is dissolved in 250 ml of hexane:ethyl acetate (1:1) and absorbed on a column of 250 g of silica gel. The column is eluted as follows:

| Fractions 1-10 | 200 ml/fraction | eluant hexane:ethyl acetate (1:1) |
| Fractions 11-18 | 250 ml/fraction | eluant hexane:ethyl acetate (7:13) |
| Fractions 19-20 | 250 ml/fraction | eluant ethyl acetate |

Fractions 13-20 are combined giving 4.29 g of solid which is dissolved in 20 ml of chloroform and added slowly to rapidly stirred petroleum ether (b.p. 35°-60° C.). The resulting precipitate is collected by filtration, dried in vacuo at 68°-72° C. and rechromatographed as described above giving [glc 1α,4 (glc 1α,4)$_5$ glc tricosaacetate].

A 6.5 g portion of [glc 1α,4 (glc 1α,4)$_5$ glc tricosaacetate] is dissolved in 6.5 ml of glacial acetic acid with stirring for one hour. The mixture is cooled to 0°-5° C. in an ice bath and a chilled 65 ml solution of 30-32% hydrogen bromide in glacial acetic acid is added with stirring. After standing for 2 hours in the ice bath, 400 ml of chilled chloroform is added and the mixture is added with vigorous stirring to one liter of ice cold aqueous sodium bicarbonate solution. The organic layer is separated, washed with a solution of sodium bisulfite, then saturated aqueous sodium bicarbonate solution followed by two water washes, dried over magnesium sulfate, filtered and the solvent removed in vacuo giving [1-bromo glc 1α,4 (glc 1α,4)$_5$ glc peracetate].

A mixture of 1.34 g of [ditrityl peracetyl glc 1α,1α′ glc], 3 g of anhydrous calcium sulfate and 30 ml of nitromethane is stirred and cooled in an ice bath to 0°-5° C. A 900 mg portion of silver triflate is added followed by 6.85 g of [1-bromo glc 1α,4 (glc 1α,4)$_5$ glc peracetate] dissolved in 20 ml of nitromethane. The mixture is stirred at 0°-5° C. for one hour, diluted with dichloromethane, filtered and the precipitate is washed with dichloromethane. The combined filtrate and washing is washed twice with saturated aqueous sodium bicarbonate, twice with water, dried over magnesium sulfate, filtered and the solvent evaporated in vacuo. The residue is dissolved in 90 ml of pyridine and 60 ml of acetic anhydride and allowed to stand for 18 hours. The mixture is then added to 1.5 liters of ice and water, stirred for one hour, filtered and the precipitate is washed with 500 ml of water. After partially drying, the solid is dissolved in 350 ml of chloroform, the organic layer is dried over magnesium sulfate, filtered and the solvent removed in vacuo at 45° C. giving an off-white glassy foam. This foam is chromatographed on a 400 g silica gel column collecting fractions of 400 ml as follows:

Fractions 1-8 Eluant 40% ethylacetate in hexane
Fractions 9-12 Eluant 50% ethylacetate in hexane
Fractions 13-16 Eluant 60% ethylacetate in hexane
Fractions 17-20 Eluant 75% ethylacetate in hexane
Fractions 21-24 Eluant 80% ethylacetate in hexane
Fractions 25-29 Eluant Ethyl acetate Fractions 23-29 are combined and dry column chromatographed. The products are located by thin-layer chromatography. Cuts 4-5″ contain pure [glc 1α,4 (glc 1α,4)$_5$ glc 1β,6 glc 1α,1α′ glc 1β,6 glc (glc 1α,4)$_5$ 1α,4 glc pentacontaacetate], m.p. 125°-130° C.

Cuts 9-10″ contain pure [glc 1α,4 (glc 1α,4)$_5$ glc 1β,6 glc 1α,1α′ lc nonacosaacetate], m.p. 99°-104° C.

EXAMPLE 18

[Glc 1α,4 (glc 1α,4)$_5$ glc 1β,6 glc 1α,1α′ glc 1β,6 glc (glc 1α,4)$_5$ 1α,4 glc]

A 200 mg portion of [glc 1α,4 (glc 1α,4)$_5$ glc 1β,6 glc 1α,1α′ glc 1β,6 glc (glc 1α,4)$_5$ 1α,4 glc pentacontaacetate] is dissolved in a mixture of 2 ml of methanol and 4 ml of methanol saturated with ammonia. The mixture is stirred at room temperature overnight and the solvents are removed in vacuo at 45° C. Additional methanol is added and then evaporated. The residue is dissolved in a mixture of 9 ml of methanol and one ml of water, filtered and added to 100 ml of anhydrous ether. The solid is recovered by filtration, washed with 50 ml of ether and dried in vacuo at room temperature overnight giving the desired product as a white amorphous solid.

EXAMPLE 19

[Glc 1α,4 (glc 1α,4)$_5$ glc 1β,6 glc 1α,1α′ glc 1β,6 glc (glc 1α,4)$_5$ 1α,4 glc, pentacontakis (H-sulfate), pentacontasalt with trimethylamine]

A 276 mg portion of trimethylamine-sulfur trioxide and 86 mg of [glc 1α,4 (glc 1α,4)$_5$ glc 1β,6 glc 1α,1α′ glc 1β,6 glc (glc 1α,4)$_5$ 1α,4 glc] in one ml of dry dimethylformamide are reacted as described in Example 3, giving the desired product as an off-white amorphous solid.

EXAMPLE 20

[Glc 1α,4 (glc 1α,4)₅ glc 1β,6 glc 1α,1α' glc 1β,6 glc (glc 1α,4)₅ 1α,4 glc, pentacontakis (H-sulfate), pentacontasodium salt]

A 120 mg portion of [glc 1α,4 (glc 1α,4)₅ glc 1β,6 glc 1α,1α' glc 1β,6 glc (glc 1α,4)₅ 1α,4 glc, pentacontakis (H-sulfate), pentacontasalt with trimethylamine] is reacted with 2.4 ml of water and one ml of 30% aqueous sodium acetate as described in Example 4, giving the desired product as a white amorphous solid.

EXAMPLE 21

[Glc 1α,4 (glc 1α,4)₅ glc 1β,6 glc 1α,1α' glc]

An 800 mg portion of [glc 1α,4 (glc 1α,4)₅ glc 1β,6 glc 1α,1α' glc nonacosaacetate] in 8 ml of methanol and 16 ml of methanol saturated with ammonia is reacted as described in Example 18, giving the desired product as a white amorphous solid.

EXAMPLE 22

[Glc 1α,4 (glc 1α,4)₅ glc 1β,6 glc 1α,1α' glc, nonacosakis (H-sulfate), nonacosasalt with trimethylamine]

A 200 mg portion of [glc 1α,4 (glc 1α,4)₅ glc 1β,6 glc 1α,1α' glc], 656 mg of trimethylamine-sulfur trioxide and 2 ml of dry dimethylformamide are reacted as described in Example 3, giving the desired product as an off-white amorphous solid.

EXAMPLE 23

[glc 1α,4 (glc 1α,4)₅ glc 1β,6 glc 1α,1α' glc, nonacosakis (H-sulfate), nonacosasodium salt]

A 400 mg portion of [glc 1α,4 (glc 1α,4)₅ glc 1β,6 glc 1α,1α' glc nonacosakis (H-sulfate), nonacosasalt with trimethylamine] is reacted with 4 ml of water and 2 ml of 30% aqueous sodium acetate as described in Example 4, giving the desired product as an off-white amorphous solid.

EXAMPLE 24

Preparation of Compressed Tablet

| Ingredient | mg/Tablet |
|---|---|
| Active Compound | 0.5–500 |
| Dibasic Calcium Phosphate NF | qs |
| Starch USP | 40 |
| Modified Starch | 10 |
| Magnesium Stearate USP | 1–5 |

EXAMPLE 25

Preparation of Compressed Tablet—Sustained Action

| Ingredient | mg/Tablet |
|---|---|
| Active Compound as Aluminum Lake*, Micronized | 0.5–500 (as acid equivalent) |
| Dibasic Calcium Phosphate NF | qs |
| Alginic Acid | 20 |
| Starch USP | 35 |
| Magnesium Stearate USP | 1–10 |

*Complement inhibitor pluis aluminum sulfate yields aluminum complement inhibitor. Complement inhibitor content in aluminum lake ranges from 5–30%

EXAMPLE 26

Preparation of Hard Shell Capsule

| Ingredient | mg/Capsule |
|---|---|
| Active Compound | 0.5–500 |
| Lactose, Spray Dried | qs |
| Magnesium Stearate | 1–10 |

EXAMPLE 27

Preparation of Oral Liquid (Syrup)

| Ingredient | % W/V |
|---|---|
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 28

Preparation of Oral Liquid (Elixir)

| Ingredient | % W/V |
|---|---|
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 29

Preparation of Oral Suspension (Syrup)

| Ingredient | % W/V |
|---|---|
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 30

Preparation of Injectable Solution

| Ingredient | % W/V |
|---|---|
| Active Compound | 0.05–5 |
| Benzyl Alcohol NF | 0.9 |
| Water for Injection | 100.0 |

EXAMPLE 31

Preparation of Injectable Oil

| Ingredient | % W/V |
|---|---|
| Active Compound | 0.05–5 |
| Benzyl Alcohol | 1.5 |

-continued

| Ingredient | % W/V |
|---|---|
| Sesame Oil qs ad | 100.0 |

EXAMPLE 32

Preparation of Intra-Articular Product

| Ingredient | Amount |
|---|---|
| Active Compound | 2–20 mg |
| NaCl (physiological saline) | 0–9% |
| Benzyl Alcohol | 0.9% |
| Sodium Carboxymethylcellulose | 1.5% |
| pH adjusted to 5.0–7.5 | |
| Water for Injection qs ad | 100% |

EXAMPLE 33

Preparation of Injectable Depo Suspension

| Ingredient | % W/V |
|---|---|
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol NF | 0.9 |
| HCl to pH 6–8 | qs |
| Water for Injection qs ad | 100.0 |

EXAMPLE 34

Preparation of Dental Paste

| Ingredient | % W/W |
|---|---|
| Active Compound | 0.05–5 |
| Zinc Oxide | 15 |
| Polyethylene Glycol 4000 USP | 50 |
| Distilled Water qs | 100 |

EXAMPLE 35

Preparation of Dental Ointment

| Ingredient | % W/W |
|---|---|
| Active Compound | 0.05–5 |
| Petrolatum, White USP qs | 100 |

EXAMPLE 36

Preparation of Dental Cream

| Ingredient | % W/W |
|---|---|
| Active Compound | 0.05–5 |
| Mineral Oil | 50 |
| Beeswax | 15 |
| Sorbitan Monostearate | 2 |
| Polyoxyethylene 20 Sorbitan Monostearate | 3 |
| Methyl Paraben USP | 0.18 |
| Propyl Paraben USP | 0.02 |
| Distilled Water qs | 100 |

EXAMPLE 37

Preparation of Topical Cream

| Ingredient | % W/W |
|---|---|
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 38

Preparation of Topical Ointment

| Ingredient | % W/W |
|---|---|
| Active Compound | 0.05–5 |
| Cholesterol | 3 |
| Stearyl Alcohol | 3 |
| White Wax | 8 |
| Petrolatum, White USP qs | 100 |

EXAMPLE 39

Preparation of Spray Lotion (Non-aerosol)

| Ingredient | % W/W |
|---|---|
| Active Compound | 0.05–5 |
| Isopropyl Myristate | 20 |
| Alcohol (Denatured) qs | 100 |

EXAMPLE 40

Preparation of Buccal Tablet

| Ingredient | mg/Tablet |
|---|---|
| Active Ingredient | 3.25 |
| 6 × Sugar | 290.60 |
| Acacia | 14.53 |
| Soluble Starch | 14.53 |
| F.D. & C. Yellow No. 6 Dye | 0.49 |
| Magnesium Stearate | 1.60 |
| | 325.00 |

The final tablet will weigh about 325 mg and may be compressed into buccal tablets in flat faced or any other tooling shape convenient for buccal administration.

EXAMPLE 41

Preparation of Lozenge

| Ingredient | g/Lozenge |
|---|---|
| Active Ingredient | 0.0140 |
| Kompact ® Sugar (Sucrest Co.) | 0.7138 |
| 6 × Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into ⅝" flat based lozenge tooling. Other shapes may also be utilized.

The compounds of the present invention may be administered internally, e.g., orally, intra-articularly or parenterally, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as nontoxic pharmaceutically acceptable diluents or carriers. The tablets or pills of novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate nontoxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term "dosage form," as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention is indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by the following identified tests: (i) Test Code 026 (C1 inhibitor)—This test measures the ability of activated human C1 to destroy fluid phase human C2 in the presence of C4 and appropriate dilutions of the test compound. An active inhibitor protects C2 from C1 and C4; (ii) Test Code 035 (C3–C9 inhibitor)—This test determines the ability of the late components of human complement (C3–C9) to lyse EAC 142 in the presence of appropriate dilutions of the test compound. An active inhibitor protects EAC 142 from lysis by human C3–C9; (iii) Test Code 036 (C-Shunt inhibitor)—In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Cap 50 Test—Here, appropriate amounts of the test compound are added to a pool of guinea pig serum in vitro, after which the undiluted serum capillary tube assay of U.S. Pat. No. 3,876,376 is run. The concentration of compound inhibiting 50% is reported; and (v) Guinea Pig Intraperitoneal Test (GPIP)—Guinea pigs weighing about 300 g are dosed intraperitoneally (i.p.) with 200 mg/kg of the test compound dissolved in saline and adjusted to pH 7–8. Approximately 0.4 ml blood samples, taken by orbital sinus puncture 30 minutes and one hour after injections, are collected directly into centrifuge tubes; 5 ml blood samples, taken by decapitation 2 hours after injection are collected directly into beakers. The samples are allowed to clot, centrifuged, and the resultant sera are assayed for complement activity using the capillary complement assay. Percent inhibition is calculated by comparison with simultaneous controls. The results of the GPIP appear in Table I together with results of test code 026, 035, 036 and Cap 50. Table I shows that the principal compounds of the invention possess highly significant complement inhibiting activity in warm-blooded animals.

TABLE I
Biological Activities

| Compound | Cl 026* Wells | C-Late 035* Wells | C-Shunt Inhibition 036* Wells | Cap 50 | In vivo activity (Guinea Pigs) % Inhibition Intraperitoneal Time (Minutes) | | |
|---|---|---|---|---|---|---|---|
| | | | | | 30 | 60 | 120 |
| Gal $1\beta,6 \to$ glc $1\alpha,1\alpha' \to$ glc $1\beta,6 \to$ gal, tetradecakis (H—sulfate), tetradecasalt with trimethylamine | 9** | | 5 | 312 | | | |
| Gal $1\beta,6 \to$ glc $1\alpha,1\alpha' \to$ glc $1\beta,6 \to$ gal, tetradecakis (H—sulfate), tetradecasodium salt | 9 | | 6 | 126 | 61 | 69 | 78 |
| Xyl $1\beta,6 \to$ glc $1\alpha,1\alpha' \to$ glc $1\beta,6 \to$ xyl, dodecakis (H—sulfate), dodecasalt with trimethylamine | 10 | | 3 | 113 | | | |
| Xyl $1\beta,6 \to$ glc $1\alpha,1\alpha' \to$ glc $1\beta,6 \to$ xyl, dodecakis (H—sulfate), dodecasodium salt | 11 | | 4 | 134 | 57 | 69 | 78 |
| Glc $1\alpha,4 \to$ glc $1\beta,6 \to$ glc $1\alpha,1\alpha' \to$ glc $1\beta,6 \to$ glc $1\alpha,4 \to$ glc, eicosakis (H—sulfate), eicosasalt with trimethylamine | 5 | N | N | | | | |
| Glc $1\alpha,4 \to$ glc $1\beta,6 \to$ glc $1\alpha,1\alpha' \to$ glc $1\beta,6 \to$ glc $1\alpha,4 \to$ glc, eicosakis (H—sulfate), eicosasodium salt | 10 | N | 6 | 112 | | | |
| Glc $1\alpha,4 \to$ glc $1\alpha,4 \to$ glc $1\beta,6 \to$ glc $1\alpha,1\alpha' \to$ glc $1\beta,6 \to$ glc $1\alpha,4 \to$ glc $1\alpha,4 \to$ glc, hexacosakis (H—sulfate), hexacosasalt with trimethylamine | 9 | 1 | 6 | 298 | | | |
| Glc $1\alpha,4 \to$ glc $1\alpha,4 \to$ glc $1\beta,6 \to$ glc $1\alpha,1\alpha' \to$ glc $1\beta,6 \to$ glc $1\alpha,4 \to$ glc $1\alpha,4 \to$ glc, hexacosakis (H—sulfate), hexacosasodium salt | 9 | 1 | 6 | 47 | | | |
| Glc $1\alpha,4 \to$ (glc $1\alpha,4 \to$)$_5$ glc $1\beta,6 \to$ glc $1\alpha,1\alpha' \to$ glc $1\beta,6 \to$ glc (glc $1\alpha,4 \to$)$_5$ $1\alpha,4 \to$ glc, pentacontakis (H—sulfate), pentacontasalt with trimethylamine | 10 | N | 5 | >500 | | | |
| Glc $1\alpha,4 \to$ (glc $1\alpha,4 \to$)$_5$ glc $1\beta,6 \to$ glc $1\alpha,1\alpha' \to$ glc $1\beta,6 \to$ glc (glc $1\alpha,4 \to$)$_5$ $1\alpha,4 \to$ glc, pentacontakis (H—sulfate) pentacontasodium salt | 9 | 2 | 6 | | | | |
| Glc $1\alpha,4 \to$ (glc $1\alpha,4 \to$)$_5$ glc $1\beta,6 \to$ glc $1\alpha,1\alpha' \to$ glc, nonacosakis (H—sulfate), nonacosasalt with trimethylamine | 9 | N | 5 | 199 | | | |
| Glc $1\alpha,4 \to$ (glc $1\alpha,4 \to$)$_5$ glc $1\beta,6 \to$ glc $1\alpha,1\alpha' \to$ glc, nonacosakis (H—sulfate), nonacosasodium salt | 10 | 1 | 6 | | | | |

\* = Tests identified by code herein
\*\* = Activity in wells, a serial dilution assay; higher well number indicates higher activity. The serial dilutions are two-fold.
N = Negative

We claim:
1. A compound selected from those of the formula:

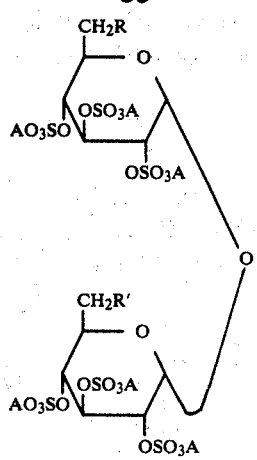

wherein A is a nontoxic pharmaceutically acceptable cation salt, wherein the salt forming moiety is selected from the group consisting of alkali metal, alkaline earth metal, ammonia and substituted ammonia selected from the group consisting of trialkylamine ($C_1$–$C_6$), piperidine, pyrazine, alkanolamine ($C_2$–$C_6$) and cycloalkylamine ($C_3$–$C_6$); R and R', when they are the same, are selected from the group consisting of

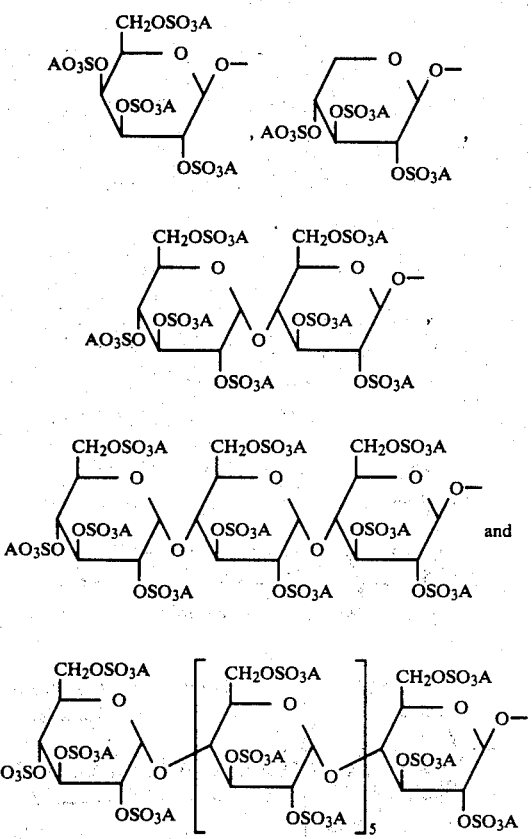

wherein A is as hereinabove defined; and R and R', when they are different, are each selected from the group consisting of —$OSO_3A$ and

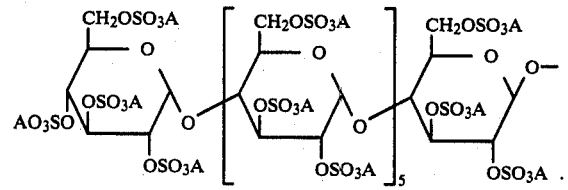

2. The compound according to claim 1, [gal 1$\beta$,6 glc 1$\alpha$,1$\alpha'$ glc 1$\beta$,6 gal, tetradecakis (H-sulfate), tetradecasalt with trimethylamine].

3. The compound according to claim 1, [gal 1$\beta$,6 glc 1$\alpha$,1$\alpha'$ glc 1$\beta$,6 gal, tetradecakis (H-sulfate), tetradecasodium salt].

4. The compound according to claim 1, [xyl 1$\beta$,6 glc 1$\alpha$,1$\alpha'$ glc 1$\beta$,6 xyl, dodecakis (H-sulfate), dodecasalt with trimethylamine].

5. The compound according to claim 1, [xyl 1$\beta$,6 glc 1$\alpha$, 1$\alpha'$ glc 1$\beta$,6 xyl, dodecakis (H-sulfate), dodecasodium salt].

6. The compound according to claim 1, [glc 1$\alpha$,4 glc 1$\beta$,6 glc 1$\alpha$,1$\alpha'$ glc 1$\beta$,6 glc 1$\alpha$,4 glc, eicosakis (H-sulfate), eicosasalt with trimethylamine].

7. The compound according to claim 1, [glc 1$\alpha$,4 glc 1$\beta$,6 glc 1$\alpha$, 1$\alpha'$ glc 1$\beta$,6 glc 1$\alpha$,4 glc, eicosakis (H-sulfate), eicosasodium salt].

8. The compound according to claim 1, [glc 1$\alpha$,4 glc 1$\alpha$,4 glc 1$\beta$,6 glc 1$\alpha$,1$\alpha'$ glc 1$\beta$,6 glc 1$\alpha$,4 glc 1$\alpha$,4 glc, hexacosakis (H-sulfate), hexacosasalt with trimethylamine].

9. The compound according to claim 1, [glc 1$\alpha$,4 glc 1$\alpha$,4 glc 1$\beta$,6 glc 1$\alpha$,1$\alpha'$ glc 1$\beta$,6 glc 1$\alpha$,4 glc 1$\alpha$,4 glc, hexacosakis (H-sulfate), hexacosasodium salt].

10. The compound according to claim 1, [glc 1$\alpha$,4 (glc 1$\alpha$,4)$_5$ glc 1$\beta$,6 glc 1$\alpha$,1$\alpha'$ glc 1$\beta$,6 glc (glc 1$\alpha$,4)$_5$ 1$\alpha$,4 glc, pentacontakis (H-sulfate), pentacontasalt with trimethylamine].

11. The compound according to claim 1, [glc 1$\alpha$,4 (glc 1$\alpha$,4)$_5$ glc 1$\beta$,6 glc 1$\alpha$,1$\alpha'$ glc 1$\beta$,6 glc (glc 1$\alpha$,4)$_5$ 1$\alpha$,4 glc, pentacontakis (H-sulfate) pentacontasodium salt].

12. The compound according to claim 1, [glc 1$\alpha$,4 (glc 1$\alpha$,4)$_5$ glc 1$\beta$,6 glc 1$\alpha$,1$\alpha'$ glc, nonacosakis (H-sulfate), nonacosasalt with trimethylamine].

13. The compound according to claim 1, [glc 1$\alpha$,4 (glc 1$\alpha$,4)$_5$ glc 1$\beta$,6 glc 1$\alpha$,1$\alpha'$ glc, nonacosakis (H-sulfate), nonacosasodium salt].

14. A compound selected from those of the formula:

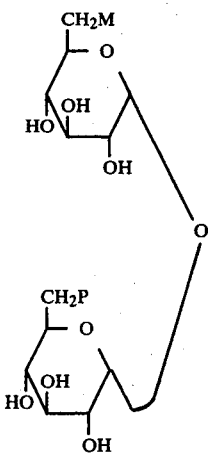

wherein M and P, when they are the same, are selected from the group consisting of

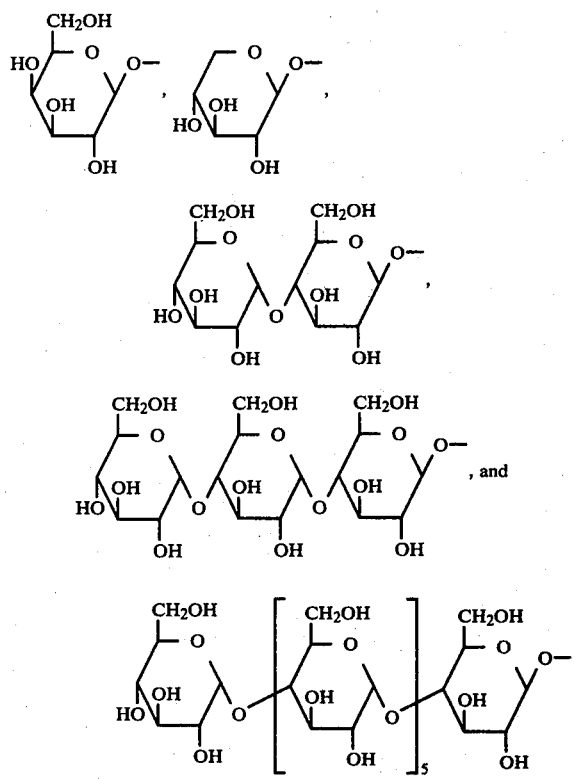

and M and P, when they are different, are each selected from the group consisting of OH and

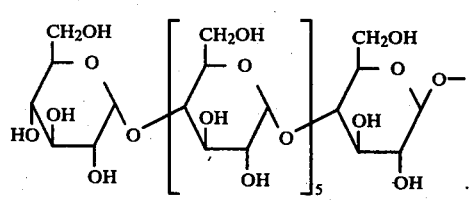

15. A method of inhibiting the complement system in a body fluid which comprises subjecting said body fluid to the action of an effective complement inhibiting amount of a pharmaceutically acceptable compound selected from those of the formula:

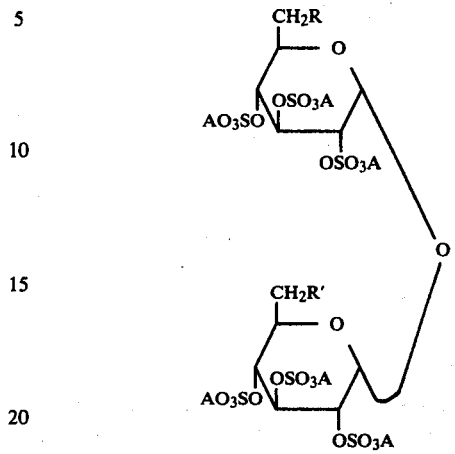

wherein A is a nontoxic pharmaceutically acceptable cation salt, wherein the salt forming moiety is selected from the group consisting of alkali earth metal, ammonia and substituted ammonia selected from the group consisting of trialkylamine ($C_1$–$C_6$), piperidine, pyrazine, alkanolamine ($C_2$–$C_6$) and cycloalkylamine ($C_3$–$C_6$); R and R', when they are the same, are selected from the group consisting of

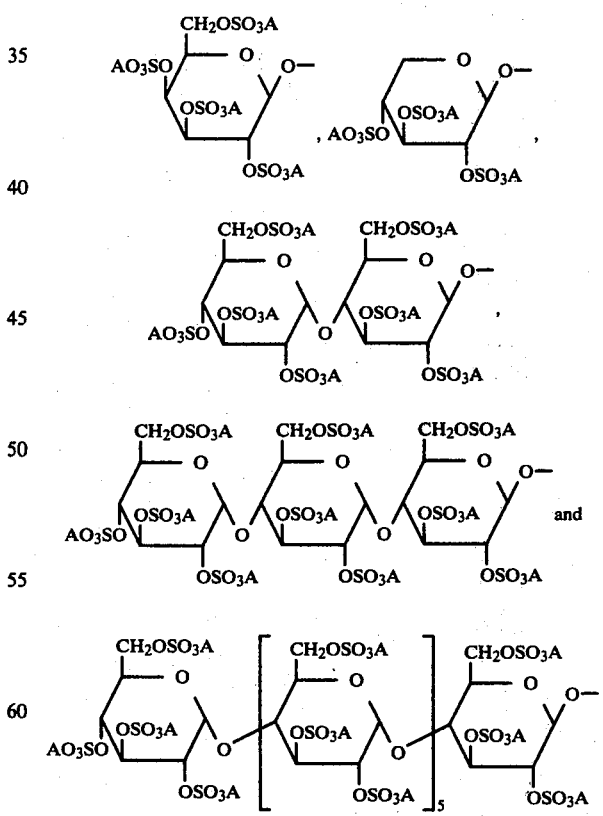

wherein A is as hereinabove defined; and R and R', when they are different, are each selected from the group consisting of —$OSO_3A$ and

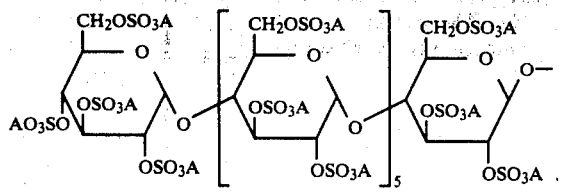

16. The method according to claim 15, wherein the body fluid is blood serum.

17. A method of inhibiting the complement system in a warm-blooded animal which comprises administering to said warm-blooded animal an effective complement inhibiting amount of a pharmaceutically acceptable compound selected from those of the formula:

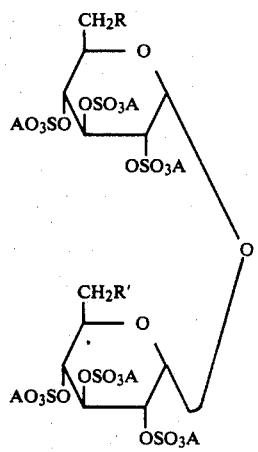

wherein A is a nontoxic pharmaceutically acceptable cation salt, wherein the salt forming moiety is selected from the group consisting of alkali metal, alkaline earth metal, ammonia and substituted ammonia selected from the group consisting of trialkylamine ($C_1$-$C_6$), piperidine, pyrazine, alkanolamine ($C_2$-$C_6$) and cycloalkylamine ($C_3$-$C_6$); R and R', when they are the same, as selected from the group consisting of

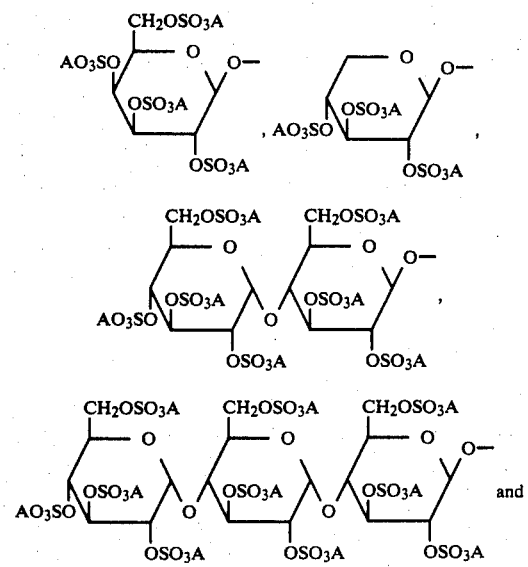

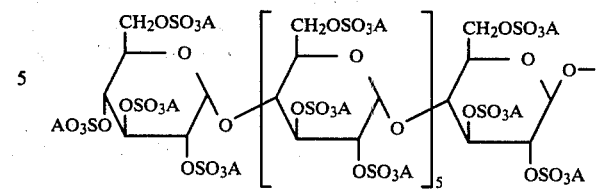

-continued

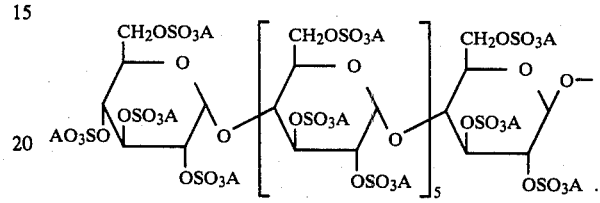

wherein A is as hereinabove defined; and R and R', when they are different, are each selected from the group consisting of —$OSO_3A$ and 18. The method according to claim 15 or 17, wherein the compound is [gal 1β,6 glc 1α,1α' glc 1β,6 gal, tetradecakis (H-sulfate), tetradecasalt with trimethylamine].

19. The method according to claim 15 or 17, wherein the compound is [gal 1β,6 glc 1α,1α' glc 1β,6 gal, tetradecakis (H-sulfate), tetradecasodium salt].

20. The method according to claim 15 or 17, wherein the compound is [xyl 1β,6 glc 1α,1α' glc 1β,6 xyl, dodecakis (H-sulfate), dodecasalt with trimethylamine].

21. The method according to claim 15 or 17, wherein the compound is [xyl 1β,6 glc 1α,1α' glc 1β,6 xyl, dodecakis (H-sulfate), dodecasodium salt].

22. The method according to claim 15 or 17, wherein the compound is [glc 1α,4 gl 1β,6 glc 1α,1α' glc 1β,6 glc 1α,4 glc, eicosakis (H-sulfate), eicosasalt with trimethylamine].

23. The method according to claim 15 or 17, wherein the compound is [glc 1α,4 glc 1β,6 glc 1α,1α' glc 1β,6 glc 1α,4 glc, eicosakis (H-sulfate), eicosasodium salt].

24. The method according to claim 15 or 17, wherein the compound is [glc 1α,4 glc 1α,4 glc 1β,6 glc 1α,1α' glc 1β,6 glc 1α,4 glc 1α,4 glc, hexacosakis (H-sulfate), hexacosasalt with trimethylamine].

25. The method according to claim 15 or 17, wherein the compound is [glc 1α,4 glc 1α,4 glc 1β,6 glc 1α,1α' glc 1β,6 glc 1α,4 glc 1α,4 glc, hexacosakis (H-sulfate), hexacosasodium salt].

26. The method according to claim 15 or 17, wherein the compound is [glc 1α,4 (glc 1α,4)₅ glc 1β,6 glc 1α,1α' glc 1β,6 glc (glc 1α,4)₅ 1α,4 glc, pentacontakis (H-sulfate), pentacontasalt with trimethylamine].

27. The method according to claim 15 or 17, wherein the compound is [glc 1α,4 (glc 1α,4)₅ glc 1β,6 glc 1α,1α' glc 1β,6 glc (glc 1α,4)₅ 1α,4 glc, pentacontakis (H-sulfate), pentacontasodium salt].

28. The method according to claim 15 or 17, wherein the compound is [glc 1α,4 (glc 1α,4)₅ glc 1β,6 glc 1α,1α' glc, nonacosakis (H-sulfate), nonacosasalt with trimethylamine].

29. The method according to claim 15 or 17, wherein the compound is [glc 1α,4 (glc 1α,4)₅ glc 1α,6 glc 1α,1α' glc, nonacosakis (H-sulfate), nonacosasodium salt].

30. The method according to claim 17, wherein the compound is administered internally.

31. The method according to claim 17, wherein the compound is administered topically.

32. The method according to claim 17, wherein the compound is administered periodontally in the oral cavity.

33. The method according to claim 17, wherein the compound is administered intra-articularly.

34. The method according to claim 17, wherein the compound is administered parenterally.

* * * * *

UNITED STATES PATENT OFFICE
CERTIFICATE OF CORRECTION

Patent No. 4,359,458  Dated November 16, 1982

Inventor(s) Vijay G. Nair, Joseph P. Joseph, Arthur J. Lewis, and Seymour Bernstein It is certified that error appears in the above-identified patent and that said Letters Patent are hereby corrected as shown below:

Claim 17: Column 37, line 43,

"...are the same, as" should read -- ...are the same, are --

Claim 29: Column 38, line 65,

"...$1\alpha,6$ glc..." should read -- ...$1\beta,6$ glc... --

Signed and Sealed this

Seventeenth Day of May 1983

[SEAL]

Attest:

DONALD J. QUIGG

Attesting Officer   Acting Commissioner of Patents and Trademarks